Figure 1:
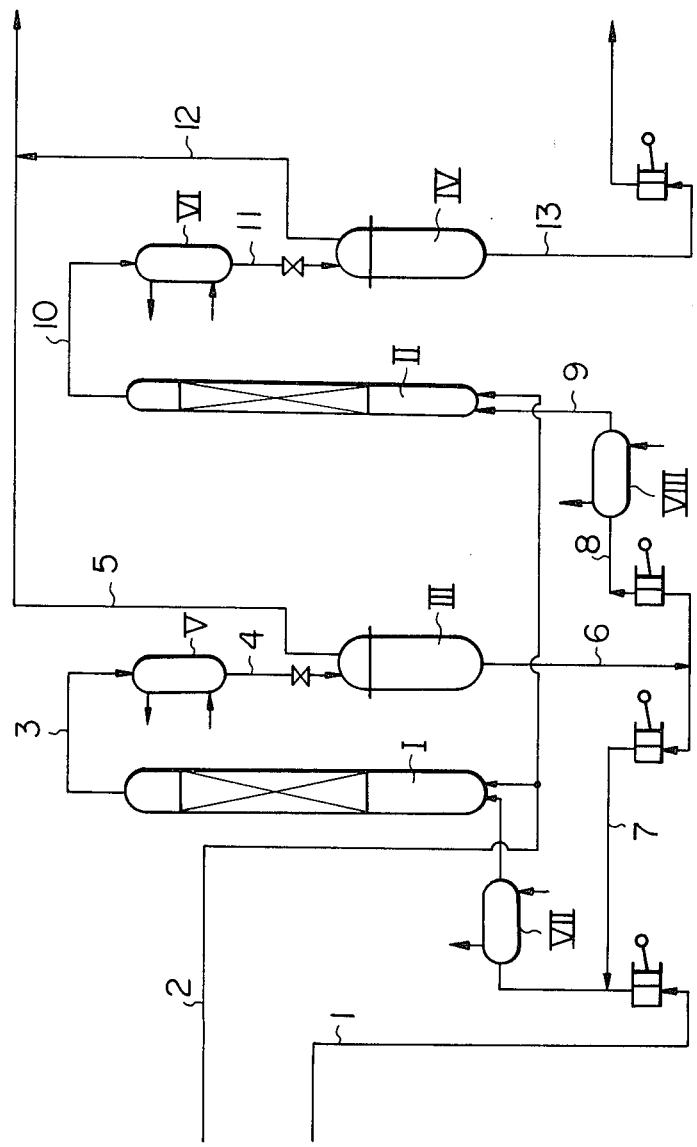

United States Patent [19]

Toriya et al.

[11] 4,010,197

[45] Mar. 1, 1977

[54] PROCESS FOR PRODUCING DIACETOXYBUTANES AND BUTANEDIOLS

[75] Inventors: Jun Toriya; Ken Shiraga, both of Kurashiki, Japan

[73] Assignee: Mitsubishi Chemical Industries Ltd., Japan

[22] Filed: Aug. 25, 1975

[21] Appl. No.: 607,482

[30] Foreign Application Priority Data

Sept. 2, 1974 Japan .............................. 49-100778

[52] U.S. Cl. ............................ 260/491; 260/497 A; 260/541; 260/635 R
[51] Int. Cl.² ................... C07C 29/00; C07C 67/28
[58] Field of Search ........................ 260/491, 635 R

[56] References Cited

UNITED STATES PATENTS 3,755,423  8/1973  Anoda et al. ................... 260/497 A
3,872,163  3/1975  Shimizu et al. .................... 260/491

*Primary Examiner*—Vivian Garner
*Attorney, Agent, or Firm*—Bierman & Bierman

[57] ABSTRACT

There is disclosed a process for producing diacetoxybutane diol by hydrogenating diacetoxybutene in the presence of a hydrogenation catalyst in which the hydrogenation is carried out in two stages within predetermined temperature ranges, the temperature of the second stage is higher than that of first thereby obtaining the product in high selectivity with high conversion, and a process for producing butanediol by hydrolyzing the diacetoxybutane thus obtained in the presence of a solid acid catalyst.

9 Claims, 2 Drawing Figures

PROCESS FOR PRODUCING DIACETOXYBUTANES AND BUTANEDIOLS

This invention relates to a process for producing diacetoxybutane by hydrogenating diacetoxybutene and the production of butanediol by hydrolysis of the diacetoxybutane thus obtained.

It has already been known that diacetoxybutene which has been obtained by reacting butadiene, acetic acid and oxygene is hydrogenated in the presence of a palladium or nickel catalyst to obtain diacetoxybutane which is hydrolized to convert into butanediol (refer to British Pat. No. 1,170,222 and U.S. Pat. No. 3,755,423). Because hydrogenation of diacetoxybutene is exothermic and the temperature range within which such hydrogenation is conveniently performed is relatively narrow, it is essential to maintain the temperature within predetermined range to avoid undesirable side-reaction. Further, the boiling points of diacetoxybutane and diacetoxybutene are nearly the same, so it is difficult to separate the two compounds by distillation. Thus, where diacetoxybutene is firstly hydrogenated and subsequently subjected to hydrolysis, it is natural that a mixture of both compounds is supplied to the hydrolysis stage; in this connection, it is important to improve the selectivity and the conversion of diacetoxybutane in order to obtain butanediol in a yield as high as possible.

We have conducted intensive studies to obtain a commercially applicable process for hydrogenation of diacetoxybutene and have found that, if hydrogenation is effected in two stages while the reaction temperatures in each stage are kept within predetermined ranges, improved efficiency of hydrogenation is achieved. We have also found that the product obtained by hydrogenation according to this invention can be directly subjected to hydrolysis to obtain butanediol; however, of course, acetic acid and butylacetate which are byproducts in hydrogenation may be previously removed, for example, by distillation.

Accordingly an object of this invention is to provide a commercially feasible process for producing diacetoxybutane by hydrogenating diacetoxybutene in the presence of a supported hydrogenation catalyst.

Another object is to provide a process for producing butanediol by hydrogenating diacetoxybutene to obtain diacetoxybutane followed by hydrolyzing it.

This object is achieved by the process according to this invention comprising hydrogenating diacetoxybutene wherein said hydrogenation is continuously effected in two reaction zones containing a supported hydrogenation catalyst, the first zone being a fixed bed type operated under adiabatic conditions, said process comprising dividing the reaction product discharged from the first zone into two portions, one being cooled and recirculated into the first zone to maintain the temperature thereof at from 50° to 150° C and the remaining portion being supplied to the second zone maintained at a temperature higher than that of the first zone thereby producing diacetoxybutane in high yield.

Another object is achieved by catalytically reacting diacetoxybutane, which has been produced by hydrogenating diacetoxybutene, with water at a temperature of from 30° to 200° C in the presence of a solid acid catalyst thereby obtaining butanediol.

This invention will be explained in detail hereinafter.

Diacetoxybutene which is the starting material according to this invention is produced by reacting in the presence of a palladium catalyst butadiene, acetic acid and molecular oxygen, optionally in the presence of a solvent, such acetoxylation being carried out according to any known process. In general, butadiene, acetic acid and oxygen or molecular oxygen-containing gas are reacted in the presence of a palladium catalyst by using any of fixed bed, fluidized bed or suspension processes.

Examples of the catalyst which may be employed for acetoxylation according to this invention include, for example, a homogeneous liquid catalyst, such as a Redox system comprising palladium salt and copper salt, and a solid catalyst of elementary metal or metal salt of Pd, Pt, Rh, Ir and Ru and a combination with a cocatalyst of elementary metal or metal salt of Cu, Ag, Zn, Ni, Cr, Fe, Co, Cd, Sn, Pb, Mo, W, Sb, Te, Se, Bi, alkali metal and alkaline earth metal; and a preferred one is a supported catalyst consisting essentially of metallic palladium and at least one cocatalyst selected from metallic bismuth, selenium, antimony and tellurium. Examples of the carrier on which catalytic ingredient(s) are supported include, for example, activated carbon, silica gel, silica-alumina, alumina, clay, bauxite, magnesia, diatomaceous earth and pumice. The amounts of metals in the catalyst to be supported on the carrier are, in general, 0.1 to 20% by weight of metallic palladium and 0.01 to 30% by weight of the cocatalyst ingredient. The acetoxylation reaction is carried out at a temperature of, in general, from 40° to 180° C, preferably 60° to 150° C and under a superatmospheric pressure.

As starting material according to this invention, there is used a mixture of diacetoxybutene isomers obtained from the acetoxylation product from which water and acetic acid, and optionally a high boiling fraction and the catalyst, have been separated, or diacetoxybutene which is isolated from such mixture by distillation separation. Thus, the starting material comprises mainly 1,4-diacetoxybutene-2 or mainly 3,4-diacetoxybutene-1, or a mixture of both, in some cases the starting material may contain acetic acid preferably in a proportion of up to 10% by weight, and may also contain a high boiling fraction so far as no catalyst for acetoxylation is present.

Hydrogen which may be used for hydrogenation according to this invention is not necessarily in pure form but may be diluted with an inert gas, such as nitrogen, or a saturated hydrocarbon, such as methane. The concentration of hydrogen is not critical and usually is more than 10% by volume and preferably more than 50%.

Carbon monoxide and carbon dioxide are poison against the hydrogenation catalyst, thus the content of such gas in hydrogen-containing gas should be reduced to as little as possible, in general, to less than 5 ppm and preferably less than 1 ppm.

Hydrogen is usually supplied from a conventional water-electrolysis or steam reforming process, but the exhaust gas from the reaction system of this invention may be used, for example, a gas which is obtained by subjecting the reaction product of this invention to gas-liquid separation may be recirculated as a hydrogen source.

Examples of the catalyst for hydrogenation which may be used in the reaction according to this invention include, for example, palladium or nickel supported catalyst in which the state of palladium or nickel is not critical. Such palladium catalyst may include various forms and, in general, metallic palladium supported on active carbon, alumina and magnesia is used. Such nickel catalyst is metallic nickel, such as Raney nickel and reduced nickel, and metallic nickel supported on a carrier together with a cocatalyst such as Zn, V, Fe, Co, Ca and Ti. Examples of the carrier for nickel catalyst include, in general, alumina, silica gel, silica-alumina, clay, bauxite, magnesia, diatomaceous earth and pumice.

Among the hydrogenation catalysts, the preferred one is metallic palladium supported on active carbon in the form of pellets of 3 to 6 mm diameter and having a specific surface area of 700 to 1,200 m²/g.

It has been found that the hydrogenation reaction proceeds in accord with "reaction of zero order" where a large amount of diacetoxybutene is present in the system, and when the concentration of diacetoxybutene drops considerably, in such a case that the conversion reaches to 80 – 90% (in case of in the absence of the solvent), the reaction proceeds in accord with "first order reaction" with the result that the reaction rate slows.

On the other hand, it has also been found that, where the hydrogenation temperature has risen at high concentration of diacetoxybutene, side-reaction occurs resulting in lowering the selectivity of diacetoxybutane but the hydrogenation product of diacetoxybutene is relatively stable at high temperature. On the basis of this knowledge, according to this invention hydrogenation reaction is carried out in a series of two reaction zones maintained under predetermined conditions.

If the hydrogenation reaction is carried out at too high a temperature the reaction rate of side-reaction, such as hydrogenolysis, increases causing lowering of the selectivity of desired diacetoxybutane; on the other hand if carried out at too low a temperature the reaction rate is not sufficient and a large amount of catalyst is required and this is not desirable.

Regarding reaction temperatures of the two reaction zones, the temperature range of the first reaction zone is to be maintained within from 50° to 150° C, preferably 60° to 130° C, and the temperature of the second reaction zone is to be maintained higher than that at the outlet of the first zone and, since at too high a temperature it causes side-reaction, the temperature is up to 200° C and preferably from 80° to 170° C.

Although the reaction pressure is not critical in either of the reaction zones, too low a reaction pressure is not desirable, since at low pressure, the reaction rate lowers but hydrogenolysis becomes predominant resulting in lowering the selectivity; on the other hand, under too high a pressure a costly reaction vessel is required. Usually a pressure of from 1 to 400 atmospheres and preferably 1 to 100 atmospheres is used.

In carrying out the hydrogenation reaction, any solvent may be used but this is not an essential requirement. The solvent to be used is not critical but includes typically, for example, a saturated aliphatic hydrocarbon, an alcohol, an ether and an ester.

By carrying out the hydrogenation of diacetoxybutene according to this invention under the above-mentioned conditions, it is possible to increase the conversions in the first and second zones to 99.5% in maximum and 99.95% or more, respectively. The conversions are calculated by the following equations.

The conversion in the first zone =

$$\left( 1 - \frac{\text{moles of DABE discharged from the first zone}}{\text{moles of DABE supplied into the first zone}} \right) \times 100(\%)$$

The conversion in the second zone =

$$\left( 1 - \frac{\text{moles of DABE discharged from the second zone}}{\text{moles of DABE supplied into the first zone}} \right) \times 100(\%)$$

Note: DABE is diacetoxybutene.

This invention will be explained referring to the accompanying FIG. 1 in which I and II are reactors, III and IV are separators, V and VI are coolers and VII and VIII are heaters. Reactor I can be any type of a fixed bed adiabatic reactor packed with the above-mentioned hydrogenation catalyst.

The raw material, diacetoxybutene, is fed into the bottom of reactor I through pipe line 1 from a supply source (not shown), after mixing with recirculating liquid supplied through pipe line 7 and, if desired, heating to a predetermined temperature in heater VII. While hydrogen-containing gas is fed into reactor I through pipe line 2 from a supply source (not shown).

The diacetoxybutene and hydrogen-containing gas to be supplied are usually maintained at a temperature of from 40° to 60° C and, after mixing with the recirculating liquid, the reaction mixture to be introduced into the reactor is controlled to a temperature of from 40° to 120° C.

Though diacetoxybutene may be directly supplied to the reactor, it is preferable to supply after mixing it with the recirculating liquid as above. Fresh hydrogen-containing gas may be directly fed into the reactor but it is preferred that the gas phase which is obtained by subjecting the reaction product to gas-liquid separation be reused after mixing with a new hydrogen feed. The reaction product discharged from reactor I is transferred through pipe line 3 to cooler V in which the product is condensed followed by transferring to separator III in which gas-liquid separation is effected. The gaseous exhaust may be fed through pipe line 5 to a waste gas treating system (not shown); alternatively, it may be reused as a hydrogen source.

A part of the liquid phase is recirculated through pipe line 7 to reactor I after subjecting it to temperature control by cooling, and the remainder is transferred to the bottom of reactor II for further hydrogenation. It is necessary to externally cool the reaction liquid to be recirculated to reactor I. The temperature of the recirculating liquid may vary depending upon various factors, for example, the amount to be recirculated, the temperature at the outlet of reactor I and the temperature of new feed diacetoxybutene. The difference between the temperatures at the inlet and outlet of reactor I is usually 5° to 90° C and preferably 5° to 50° C, the former being lower than the latter, and the reaction temperature of reactor I is maintained at from 40° to 150° C, preferably 50° to 130° C.

Alternatively, where hydrogen and diacetoxybutene are fed into reactor I downwardly and gas-liquid concurrently, a part of the liquid product is recirculated to the top of the reactor under pressure, for example by means of a pump, after subjecting the reaction product to gas-liquid separation at the bottom of the reactor, and the liquid phase to temperature control, for example, by cooling.

The amount of liquid product to be recirculated is selected within a range of usually from 0.1 to 100 parts and preferably 0.5 to 20 parts per one part of the reaction product, which is discharged from the reaction zone and then transferred to the following second hydrogenation stage. The supply of the recirculating liquid to the reactor may be effected alone or after mixing with the raw material, diacetoxybutene; further, such supply may be effected dividedly at a plurality of places in the reactor.

Reactor II may be any type of a fixed bed reactor without any specific limitation and is packed with the above-mentioned hydrogenation catalyst.

The remaining portion of the reaction liquid obtained from gas-liquid separator III and not recirculated into reactor I is supplied, after preheating in heater VIII if necessary, to the bottom of reactor II and simultaneously hydrogen-containing gas is fed to the bottom of reactor II through pipe line 2.

The reaction product discharged from the top of reactor II is fed into cooler VI through pipe line 10 and into a separator IV in which gas and liquid are separated; then the gaseous exhaust is recovered and reused through pipe line 12 or transferred into a waste gas treating system (not shown), while the liquid phase is fed through pipe line 13 into either a purification system (not shown) in which the desired product is recovered or hydrolysis stage of the hydrogenation product (not shown).

Since the heat of reaction generated in reactor II is very small, it is not necessary to provide an external circulating cooling means but such may be provided, if desired. The temperature at which the reaction in this reactor is conducted is in general up to 200° C, and preferably from 80° to 170° C, and is to be maintained higher than that of reactor I.

Alternatively, heater VIII is omitted from FIG. 1 and the liquid reaction product discharged from reactor I can be, after separating the gas phase therefrom, directly fed into reactor II in which the required reaction temperature will be maintained by the heat generated by exothermal reaction.

The way by which the raw materials for reactors I and II are supplied is preferably, as mentioned above, upward supply of gas and liquid concurrently but may be, of course, downward and concurrent supply or gas-liquid countercurrent supply in which the liquid material (the recirculating liquid and diacetoxybutene) is downward supply and gas is upward supply.

Hydrogen-containing gas may be supplied separately to reactors I and II or alternatively continuously in series to each of the reactors and then recycled through the whole system. In the latter case, the reaction pressure of the reactor in which hydrogen is firstly supplied is maintained higher than that of the second reactor.

Reactor I and II are not necessarily independent but may be a single fixed bed and adiabatic type reactor provided with two reaction zones.

As explained above, according to this invention, hydrogenation of diacetoxybutene is effected in a multi-stage reaction zone under predetermined conditions whereby the conversion of hydrogenation takes place with high efficiency. That is, in the first stage, the reaction is carried out at 50° to 150° C by removing the heat of reaction by external cooling, and a conversion rate of 80 to 99.5% is achieved, thereby enabling the reaction to proceed rapidly and in accord with the reaction of zero order and to prevent side-reaction by operating at a lower temperature to increase the selectivity. In the second stage, the reaction proceeds in accord with the reaction of first order at low concentration of diacetoxybutene but at high reaction temperature to achieve high conversion of 99.95% or more since the product is stable at a high temperature.

The diacetoxybutane thus obtained is subjected to a catalytic hydrolysis by passing through a fixed bed packed with a solid acid catalyst. Examples of the solid acid catalyst include such as silica-alumina, activated clay, silica and a cation exchange resin, especially cation exchange resin is preferred in virtue of its higher rate of hydrolysis and lower production of undesirable byproduct such as tetrahydrofuran. Among the cation exchange resins, a sulfonic acid type strong cation exchange resin the matrix of which is a copolymer of styrene and divinyl benzene is preferred but other gel and porous type such cation exchange resins can also be used; examples of the preferred resin are available from Mitsubishi Chemical Industries Ltd., Tokyo, Japan under trade names of DIAION SK1B, SK103, SK106, PK206, PK216 and PK228. The temperature at which the hydrolysis is effected is usually from 30° to 120° C and preferably 40° to 100° C. Departing from this range, at too low a temperature the reaction rate is unacceptably low requiring a large amount of the catalyst; on the other hand at too high a temperature, the production of undesirable by-product, such as tetrahydrofuran and dihydrofuran increases lowering the yield of the object compound. That is, for example, where diacetoxybutane is hydrolyzed using DIAION SK1B resin as the catalyst at a temperature of below 100° C there is produced tetrahydrofuran of about 5% on the basis of butanediol and at 120° C 23%, whereas at a temperature of above 140° C there is produced equal or more tetrahydrofuran to butanediol. Another reason for selection of such temperature range is to prevent degradation and elution of the cation exchange resin.

The hydrolysis pressure is not critical but the pressure preferred is such that the boiling of the reaction mixture and/or bubbling of the dissolved gas are prevented; in general, the pressure used is in the range of from atmospheric to 10 kg/am²G.

Water is one of the reactants for the hydrolysis and is also a solvent, so the proportion of water used is more than the stoichiometric amount. In order to smoothly carry out the hydrolysis, it is preferable to carry out the reaction in a homogeneous liquid phase. If a large excess of water is used, the raw material, acetoxybutane, will dissolve in water completely to form a homogeneous liquid phase and further the larger the amount of water used the easier it is to increase the conversion into butanediol; but an excess of water requires a large amount of energy in the recovery of butanediol from the reaction product. On the other hand, too small an amount of water results in lowering of the conversion causing a difficulty in recovery of butanediol. Thus, it has been found that a suitable range of the molar proportion of water to diacetoxybutane is usually 2 to 100 : 1 and preferably 4 to 50 : 1.

Where the hydrolysis product is subjected to a distillation operation to recover the desired product of butanediol, if the concentration of acetic acid increases there is observed reverse reaction, that is, esterification reaction between acetic acid and butanediol lowering the yield of the desired product. Therefore, it is preferred to firstly and simultaneously remove substantially all of the water and acetic acid and subject the product to distillation to separate unreacted diacetoxybutane and partially hydrolyzed product, monohydroxy acetoxybutane. Then butanediol is recovered by rectification.

According to this invention, it is possible to achieve the conversion in hydrogenation of diacetoxybutene of as high as 99.95% or more and to decrease the content of butenediol in the hydrolysis product to a minimum. The recovery of butanediol is satisfactorily performed in a rectifying column having a number of theoretical plates of up to 90 plates and a reflux ratio of up to 10. The unreacted material and the partially hydrolyzed product i.e. (diacetoxybutane and monohydroxy acetoxybutane) may be recirculated to the hydrolysis stage, if desired.

This invention will be explained by means of Examples; however, it should be understood that this invention is in no way limited by these Examples.

EXAMPLE 1

The reaction was carried out in an apparatus as illustrated in FIG. 1. Each reactor, I and II, was made of stainless steel of SUS 316 of 32.9 mm internal diameter and 1500 mm length packed with 430 g of a hydrogenation catalyst. The catalyst was metallic palladium (2.0 wt% for the carrier) supported on γ-alumina which had been shaped into a cylinder 3 mm in diameter and 3 mm long, the bulk density of the catalyst being 0.98 kg/l. The raw material, diacetoxybutene, contained more than 98% by weight of 1,4-diacetoxybutene-2 and was obtained by distillation purification of the reaction product produced by acylation reaction of butadiene, acetic acid and oxygen at 80° to 100° C in the presence of palladium catalyst.

Into the bottom of reactor I maintained at a reaction pressure of 10 kg/cm² were introduced hydrogen (purity being more than 99.9%) at a rate of 200 Nl/hr. and diacetoxybutene at a rate of 86 g/hr., which had been mixed with recirculating liquid reaction product at a rate of 0.75 l/hr. and preheated to 75° C in heater VII. The reacted liquid discharged from the top of reactor had a temperature of 104° C. The reacted liquid was cooled in cooler V followed by passing through a valve in which the pressure was dropped to normal pressure and then to separator III to effect separation of gas and liquid, the gas phase then being purged to a waste gas treating system. Part of the liquid reaction product was preheated to 110° C in heater VIII and introduced at a rate of 87 g/hr. to the bottom of reactor II maintained under reaction pressure of 10 kg/cm²G, while the remaining portion was recirculated into reactor I. At the same time, hydrogen (purity being more than 99.9%) was supplied into the bottom of reactor II at a rate of 200 Nl/hr.

The reaction product discharged from the top of reactor II had a temperature of 110° C and was cooled in cooler VI followed by dropping the pressure to normal pressure in a valve and separating gas and liquid in separator IV, then the object material was recovered from the liquid phase. As the result, the conversion of 1,4-diacetoxybutene-2 was approximately 100% and no unreacted 1,4-diacetoxybutene-2 was detected. The selectivity of the 1,4-diacetoxybutane produced was 99.0%.

COMPARATIVE EXAMPLE 1

The procedures similar to those of Example 1 were repeated except that there was used only reactor I packed with 860 g of the catalyst to effect the hydrogenation of 1,4-diacetoxybutene-2 in single stage. As the result, the temperature of the reaction product discharged from the top of reactor was 107° C, the conversion of 1,4-diacetoxybutene-2 was 99.0% and 1,4-diacetoxybutane was obtained in a selectivity of 99.1%.

COMPARATIVE EXAMPLE 2

According to the procedures similar to those of Comparative Example 1, 1,4-diacetoxybutene-2 was hydrogenated except that the temperature at the inlet of reactor I was 105° C. Then, the temperature of the product discharged from reactor I was 135° C, the conversion of 1,4-diacetoxybutene was 99.9% and 1,4-diacetoxybutane was obtained with a selectivity of 96.3%.

EXAMPLE 2

The procedures similar to those of Example 1 were repeated excepting that the raw material contained 70% by weight of 3,4-diacetoxybutene-1 with the balance being 1,4-diacetoxybutene-2. In this case, the temperature of the reaction product discharged from reactor I was 102° C, the temperature at the inlet of reactor II was 110° C and the temperature of the reaction product discharged from reactor II was 115° C. No unreacted diacetoxybutene in the product was detected, the conversion of diacetoxybutenes was approximately 100% and the selectivity of 1,4-diacetoxybutane was 98.3%.

EXAMPLE 3

Figure 2:
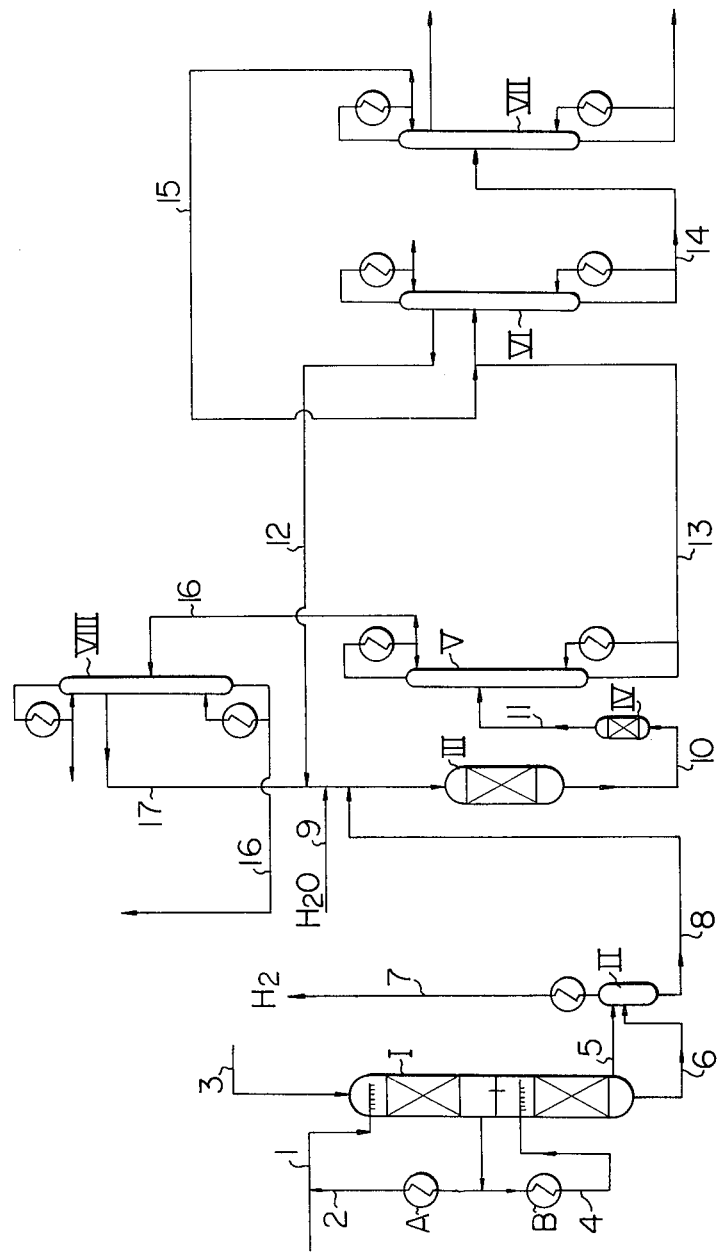

In this Example, the hydrogenation of diacetoxybutene and the hydrolysis of diacetoxybutane were carried out in an apparatus illustrated in accompanying FIG. 2.

Reactor I had dimensions of 1,000 mm internal diameter and 15,000 mm length and a lining of stainless steel of SUS316, and was provided with four catalyst beds each of which was 1,500 mm in length and packed with 800 kg of catalyst of 1% by weight of metallic palladium supported on active carbon in the form of pellet of 3 to 4 mm.

Within reactor I, a means for separating gas and liquid was provided between the second catalyst bed and the third catalyst bed; thus the first and second catalyst beds constituted the first reaction zone and the third and fourth beds were the second reaction zone.

Diacetoxybutene to be supplied to the reactor was previously prepared by reacting butadiene, acetic acid and molecular oxygen-containing gas in the presence of a palladium catalyst and removing from the reaction product by distillation the fraction boiling at a temperature lower than the boiling point of acetic acid followed by rectifying under an overhead pressure of 10 mmHg, and comprised 90.8% by weight of 1,4-diacetoxybutene-2, 8.7% of 3,4-diacetoxybutene-1, 0.4% of medium boiling fraction and 0.6% of high boiling fraction.

To the top of reactor I were supplied (1) through pipe line 1 at a rate of 4075 kg/hr, the above-mentioned diacetoxybutene to which was added through pipe line 2 at a rate of 40823 kg/hr the liquid product recovered from the first zone of reactor I and separated from the gaseous phase, while the temperature and the pressure of the mixed diacetoxybutene were maintained at 60° C and under 90 kg/cm$^2$G and (2) hydrogen feed (H$_2$: 95%, CH$_4$:5%, CO:1 ppm and CO$_2$; 3 ppm, by volume) through pipe line 3 at a rate of 77 kg/hr and at a temperature of 60° C.

The reaction product of the first reaction zone from which the gaseous phase had been separated in the separation means provided between the first and second zone was divided into two portions, one of which was recirculated as the diacetoxybutene feed after cooling in heat-exchanging means A and the other was fed to the upper portion of the third catalyst bed at a rate of 4123 kg/hr through pipe line 4 after heating to 110° C in heat exchanging means B. The pressure of the second reaction zone was maintained under that of the first zone. The temperature at the bottom of reactor I was 110.3° C at which temperature the liquid product and the gaseous phase were separated and the pressures thereof were allowed to drop to normal pressure. Then, both products were fed through pipe lines 5 and 6 to separator II in which the liquid product and gaseous phase were further separated. The gaseous phase which was hydrogen containing about 50% by volume of methane was released at a rate of 29 kg/hr through pipe line 7. While the reaction product was recovered at a rate of 4123 kg/hr from the separator the main component of which was diacetoxybutane containing 1.0% of acetic acid, 2.4% of medium boiling fraction (mainly butylacetate), 8.5% of 1,2-diacetoxybutane, 0.06% of high boiling fraction, less than 10 ppm of 3,4-diacetoxybutene and less than 50 ppm of 1,4-diacetoxybutene, by weight, the yield of 1,4-diacetoxybutane being about 97% on the basis of the raw material 1,4-diacetoxybutene.

To hydrolysis column III of 3,000 mm inner diameter and 10 m length which was made of stainless steel and packed with 50 m$^3$ of cation exchange resin (available from Mitsubishi Chemical Industries Limited, Tokyo, Japan, under the name of DIAION SK1B H type) were supplied (1) the liquid diacetoxybutane recovered from separator II through pipe line 8, (2) the recirculating liquid recovered through pipe line 12 from recovery column VI at a rate of 7,708 kg/hr (3) fresh through pipe throughpipe line 9 at a rate of 200 kg/hr and (4) water recovered through pipe line 17 from water/acetic acid separator VIII at a rate of 7,068 kg/hr; the mixed feed stock being maintained at a temperature of 60° C. The hydrolysis reaction product was recovered at a rate of 19,099 kg/hr and fed through pipe line 10 to a purification column IV packed with 5 m$^3$ of an anion exchange resin thereby effecting the removal of sulfonate ion which was eluted from the cation exchange resin. Then the product was fed through pipe line 11 to deacetic acid column V of 2,800 mm diameter and 5 m length wich was made of stainless steel of SUS316 and having 10 bubble plates and was operated under conditions of 100 torrs. overhead pressure, 190° C bottom temperature and 0.1 reflux ratio to obtain a distillate containing acetic acid at a rate of 9,115 kg/hr and a bottom containing the desired product at a rate of 9.984 kg/hr.

The bottom was fed through pipe line 13 together with a side cut recovered through pipe line 15 from a rectifying column VII to a recovery column VI of 2,900 mm internal diameter and 25 m length which was made of stainless steel of SUS304 and provided with 60 bubble trays the operation conditions of which were 77 torr. overhead pressure and 80 reflux ratio thereby obtaining mixture of 1,2-diacetoxybutane, 1,2-hydroxyacetoxybutane and 1,2-butanediol at a rate of 398 kg/hr as an overhead, a crude butanediol at a rate of 1932 kg/hr as a bottom and an unreacted material containing 1,4-diacetoxybutane, 1,4-hydroxyacetoxybutane and 1,4-butanediol at a rate of 7,708 kg/hr as a side cut discharged from the fifteenth tray from the top, said side cut being recirculated into hydrolysis column III.

The bottom from the recovery column was fed through pipe line 14 to rectifying column VII which was made of stainless steel of SUS304 of 1,700 mm inner diameter and 17 m length and provided with 21 bubble trays and the operation conditions of which were 190° C bottom temperature, 100 torr. overhead pressure and 42 reflux ratio, thereby obtaining 1,4-butanediol containing tetrahydrofuran at a rate of 54 kg/hr as an overhead to be recirculated to the recovery column through pipe line 15, 1,4-butanediol containing high boiling fraction at a rate of 57 kg/hr as a bottom and the desired product of 1,4-butanediol at a rate of 1875 kg/hr as a side cut from the fourth tray from the top.

On the other hand, the overhead of deacetic acid column V was fed through pipe line 16 to water/acetic acid separator VIII which was made of stainless steel of SUS316 of 2900 mm internal diameter of a recovery portion, 2,000 mm internal diameter of a condensation portion and 34 m length and provided with 85 perforated trays, the operation conditions of which were 125° C bottom temperature and 400 torrs. overhead pressure, thereby obtaining an overhead containing tetrahydrofuran, butanol and water at a rate of 266 kg/hr, a side cut of 12% aqueous acetic acid at a rate of 7,068 kg/hr from the 20th tray from the top which was recycled through pipe line 17 to hydrolysis column III and a bottom of 1.2% aqueous acetic acid at a rate of 1,821 kg/hr which was recirculated through pipe line 16 to the acetoxylation stage (not shown).

What is claimed is:

1. In a process for producing a diacetoxybutane by hydrogenating a diacetoxybutene compound in the presence of a supported hydrogenation catalyst, the improvement which comprises,
   introducing said compound and hydrogen into a first reaction zone having said hydrogenation catalyst in a fixed bed therein, hydrogenating said compound under adiabatic conditions at a first temperature of 50° to 150° C to form a first reaction product,
   dividing said reaction product into a first portion and a second portion, cooling said first portion, recirculating said first portion to said first zone to maintain said first temperature,
   introducing said second portion and hydrogen into a second reaction zone having said hydrogenation catalyst in a fixed bed therein, further hydrogenating said second portion at a second temperature higher than said first temperature and up to 200° C.

2. A process for producing a diacetoxybutane according to claim 1, in which the reaction temperature and the reaction pressure in the first zone are 60° to 130° C and atmospheric to 100 atm. and the reaction temperature and the reaction pressure in the second zone are 80° to 170° C and atmospheric to 100 atm.

3. A process for producing a diacetoxybutane according to claim 1, in which the proportion of said divided two portions is 0.5 to 20 parts to be recirculated to the first zone per one part to be supplied to the second zone, and the portion to be recirculated is maintained at a temperature of 5° to 90° C lower than that at the outlet of the first zone.

4. A process for producing a diacetoxybutane according to claim 1, in which said supported catalyst is metallic palladium supported on active carbon having a specific surface area of from 700 to 1200 m²/g, said compound, said first reaction product and hydrogen being supplied to the tops of the first and second zones downwardly and concurrently.

5. A process for producing a diacetoxybutane according to claim 1, in which said diacetoxybutene is 1,4-diacetoxybutene-2.

6. A process for producing a diacetoxybutane according to claim 1, in which said hydrogen contains carbon monoxide and carbon dioxide in a proportion of less than 5 ppm.

7. In a process for producing a butanediol by hydrogenating a diacetoxybutene compound in the presence of a supported hydrogenation catalyst and effecting hydrolysis of the diacetoxybutane obtained, the improvement which comprises
introducing said compound and hydrogen into a first reaction zone having said hydrogenation catalyst in a fixed bed therein, hydrogenating said compound under adiabatic conditions at a first temperature of 50° to 150° C to form a first reaction product,
dividing said reaction product into a first portion and a second portion, cooling said first portion, recirculating said first portion to said first zone to maintain said first temperature,
introducing said second portion and hydrogen into a second reaction zone having said hydrogenation catalyst in a fixed bed therein, further hydrogenating said second portion at a second temperature higher than said first temperature and up to 200° C, thereby producing diacetoxybutane and effecting hydrolysis of said diacetoxybutane in the presence of a solid, acid catalyst.

8. A process for producing a butanediol according to claim 7, in which said solid acid catalyst is a sulfonic acid type cation exchange resin and said hydrolysis is effected at a temperature of from 30° to 120° C.

9. In a process for producing a butanediol by hydrogenating a diacetoxybutene compound in the presence of a supported hydrogenation catalyst and effecting hydrolysis of the diacetoxybutane obtained, the improvement which comprises
introducing said compound and hydrogen into a first reaction zone having said hydrogenation catalyst in a fixed bed therein, hydrogenating said compound under adiabatic conditions at a first temperature of 60° to 130° C and under a pressure of 1 to 100 atmospheres to form a first reaction product,
dividing said first reaction product into a first portion and a second portion, there being from 0.5 to 20 parts of said first portion to 1 part of said second portion, cooling said first portion to a temperature of 5° to 90° C lower than said first temperature, recirculating said first portion to said first zone to maintain said first temperature,
introducing said second portion and hydrogen into a second reaction zone having said hydrogenation catalyst in a fixed bed therein, further hydrogenating said second portion at a second temperature higher than said first temperature and from 80° to 170° C and under a pressure of 1 to 100 atmospheres to produce diacetoxybutane,
hydrolyzing said diacetoxybutane in the presence of a solid, acid cation exchange resin at a hydrolyzing temperature of 40° to 100° C to produce a butanediol reaction product,
distilling said butanediol product to remove water and acetic acid followed by removal of unreacted and partially hydrolyzed material, and
rectifying the butanediol product at a reflux ratio of up to 10 in a rectifier having up to 90 theoretical plates, whereby butanediol is recovered as an overhead.

* * * * *